(12) United States Patent
Garner et al.

(10) Patent No.: US 8,034,074 B2
(45) Date of Patent: Oct. 11, 2011

(54) INTRAVASCULAR FILTER RETRIEVAL DEVICE HAVING AN ACTUATABLE DILATOR TIP

(75) Inventors: Joseph Garner, Maple Grove, MN (US); Matthew L. Young, Mound, MN (US); Andrew Forsberg, Minneapolis, MN (US); Louis Ellis, St. Anthony, MN (US); Gary Hendrickson, Big Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 962 days.

(21) Appl. No.: 11/616,612

(22) Filed: Dec. 27, 2006

(65) Prior Publication Data

US 2007/0106324 A1 May 10, 2007

Related U.S. Application Data

(63) Continuation of application No. 10/083,810, filed on Feb. 27, 2002, now Pat. No. 7,226,464.

(60) Provisional application No. 60/272,657, filed on Mar. 1, 2001.

(51) Int. Cl.
*A61M 29/00* (2006.01)
(52) U.S. Cl. .................................................. 606/200
(58) Field of Classification Search .............. 606/194, 606/192, 198, 200; 623/1.11
See application file for complete search history.

(56) References Cited

U.S. PATENT DOCUMENTS

| | | |
|---|---|---|
| 3,472,230 A | 10/1969 | Fogarty |
| 3,952,747 A | 4/1976 | Kimmell, Jr. |
| 3,996,938 A | 12/1976 | Clark, III |
| 4,425,908 A | 1/1984 | Simon |
| 4,643,184 A | 2/1987 | Mobin-Uddin |
| 4,662,885 A | 5/1987 | DiPisa, Jr. |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,857,045 A | 8/1989 | Rydell |
| 4,873,978 A | 10/1989 | Ginsburg |
| 4,886,061 A | 12/1989 | Fischell et al. |
| 4,969,891 A | 11/1990 | Gewertz |

(Continued)

FOREIGN PATENT DOCUMENTS

WO 96/01591 A1 1/1996

(Continued)

*Primary Examiner* — Tom Hughes
*Assistant Examiner* — David Eastwood
(74) *Attorney, Agent, or Firm* — Seager, Tufte & Wickhem LLC

(57) ABSTRACT

A filter retrieval device having an actuatable dilator tip for retrieval of an intravascular filter from a body lumen is disclosed. An outer shaft coupled to a distal sheath is advanced along a filter wire to desired point within the vasculature. An intravascular filter such as a distal protection filter can be advanced along the filter wire to a point distal a lesion to collect debris dislodged during a medical procedure. Disposable in part within the distal sheath is an actuatable dilator tip adapted to retrieve the filter at least in part within the distal sheath. Actuation of the dilator tip may be accomplished by any number of means, including a resilient member such as a spring coil, or by a reduced inner diameter portion disposed on the distal sheath adapted to engage a plurality of recessed surfaces disposed on the dilator tip.

7 Claims, 18 Drawing Sheets

U.S. PATENT DOCUMENTS

| | | | |
|---|---|---|---|
| 5,011,488 A | 4/1991 | Ginsburg | |
| 5,071,407 A | 12/1991 | Termin et al. | |
| 5,133,733 A | 7/1992 | Rasmussen et al. | |
| 5,147,379 A * | 9/1992 | Sabbaghian et al. | 606/206 |
| 5,160,342 A | 11/1992 | Reger et al. | |
| 5,192,286 A | 3/1993 | Phan et al. | |
| 5,275,622 A | 1/1994 | Lazarus et al. | |
| 5,324,304 A | 6/1994 | Rasmussen | |
| 5,329,942 A | 7/1994 | Gunther et al. | |
| 5,370,657 A | 12/1994 | Irie | |
| 5,405,380 A | 4/1995 | Gianotti et al. | |
| 5,415,630 A | 5/1995 | Gory et al. | |
| 5,419,774 A | 5/1995 | Willard et al. | |
| 5,462,529 A | 10/1995 | Simpson et al. | |
| 5,536,242 A | 7/1996 | Willard et al. | |
| 5,549,626 A | 8/1996 | Miller et al. | |
| 5,649,953 A * | 7/1997 | Lefebvre | 606/200 |
| 5,662,671 A | 9/1997 | Barbut et al. | |
| 5,669,933 A | 9/1997 | Simon et al. | |
| 5,681,347 A * | 10/1997 | Cathcart et al. | 606/200 |
| 5,683,451 A * | 11/1997 | Lenker et al. | 623/1.11 |
| 5,725,550 A | 3/1998 | Nadal | |
| 5,769,816 A | 6/1998 | Barbut et al. | |
| 5,772,669 A * | 6/1998 | Vrba | 623/1.11 |
| 5,779,716 A | 7/1998 | Cano et al. | |
| 5,800,457 A | 9/1998 | Gelbfish | |
| 5,800,525 A | 9/1998 | Bachinski et al. | |
| 5,807,398 A | 9/1998 | Shaknovich | |
| 5,814,064 A | 9/1998 | Daniel et al. | |
| 5,827,324 A | 10/1998 | Cassell et al. | |
| 5,833,650 A | 11/1998 | Imran | |
| 5,848,964 A | 12/1998 | Samuels | |
| 5,911,734 A | 6/1999 | Tsugita et al. | |
| 5,951,585 A * | 9/1999 | Cathcart et al. | 606/198 |
| 5,972,028 A * | 10/1999 | Rabenau et al. | 623/1.11 |
| 6,001,118 A | 12/1999 | Daniel et al. | |
| 6,066,149 A | 5/2000 | Samson et al. | |
| 6,066,158 A | 5/2000 | Engelson et al. | |
| 6,113,607 A | 9/2000 | Lau et al. | |
| 6,142,987 A | 11/2000 | Tsugita | |
| 6,152,946 A | 11/2000 | Broome et al. | |
| 6,165,179 A * | 12/2000 | Cathcart et al. | 606/108 |
| 6,168,579 B1 | 1/2001 | Tsugita | |
| 6,171,327 B1 | 1/2001 | Daniel et al. | |
| 6,179,859 B1 | 1/2001 | Bates et al. | |
| 6,183,491 B1 | 2/2001 | Lulo | |
| 6,203,561 B1 | 3/2001 | Ramee et al. | |
| 6,206,868 B1 | 3/2001 | Parodi | |
| 6,221,006 B1 | 4/2001 | Dubrul et al. | |
| 6,245,089 B1 | 6/2001 | Daniel et al. | |
| 6,254,633 B1 | 7/2001 | Pinchuk et al. | |
| 6,277,139 B1 | 8/2001 | Levinson et al. | |
| 6,325,829 B1 | 12/2001 | Schmotzer | |
| 6,344,049 B1 | 2/2002 | Levinson et al. | |
| 6,371,971 B1 | 4/2002 | Tsugita et al. | |
| 6,485,501 B1 * | 11/2002 | Green | 606/200 |
| 6,537,296 B2 | 3/2003 | Levinson et al. | |
| 6,551,341 B2 | 4/2003 | Boylan et al. | |
| 6,605,102 B1 | 8/2003 | Mazzocchi et al. | |
| 6,616,680 B1 * | 9/2003 | Thielen | 606/200 |
| 6,616,681 B2 | 9/2003 | Hanson et al. | |
| 6,743,247 B1 | 6/2004 | Levinson et al. | |
| 6,887,256 B2 | 5/2005 | Gilson et al. | |
| 6,974,468 B2 | 12/2005 | DoBrava et al. | |
| 7,094,249 B1 | 8/2006 | Broome et al. | |
| 7,150,756 B2 | 12/2006 | Levinson et al. | |
| 7,229,464 B2 | 6/2007 | Hanson et al. | |
| 7,306,618 B2 | 12/2007 | Demond et al. | |
| 7,410,491 B2 | 8/2008 | Hopkins et al. | |
| 2001/0041908 A1 * | 11/2001 | Levinson et al. | 606/200 |
| 2001/0044632 A1 | 11/2001 | Daniel et al. | |
| 2002/0095174 A1 * | 7/2002 | Tsugita et al. | 606/200 |
| 2002/0120286 A1 * | 8/2002 | DoBrava et al. | 606/200 |
| 2002/0183782 A1 | 12/2002 | Tsugita et al. | |
| 2003/0125764 A1 | 7/2003 | Brady et al. | |
| 2004/0106944 A1 | 6/2004 | Daniel et al. | |
| 2006/0004405 A1 | 1/2006 | Salahieh et al. | |
| 2007/0088384 A1 | 4/2007 | Vrba et al. | |

FOREIGN PATENT DOCUMENTS

WO      EP 0714640 A1 *   5/1996

* cited by examiner

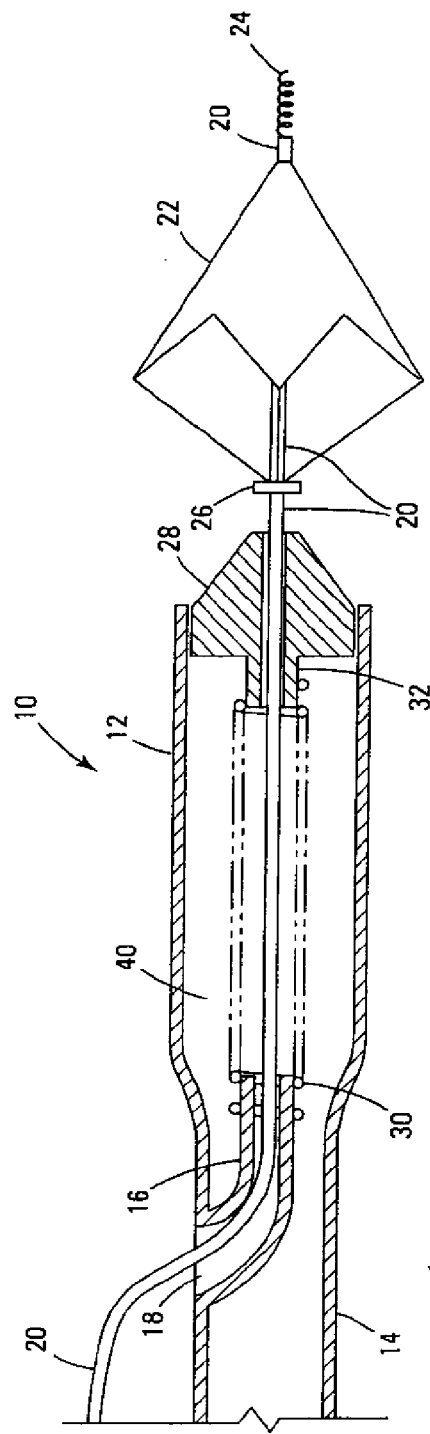
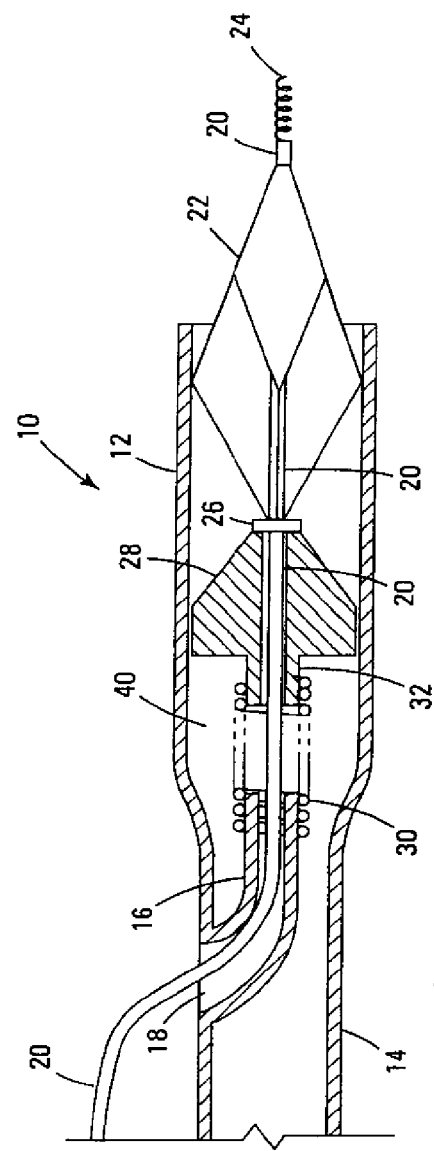
Fig. 1
Fig. 2

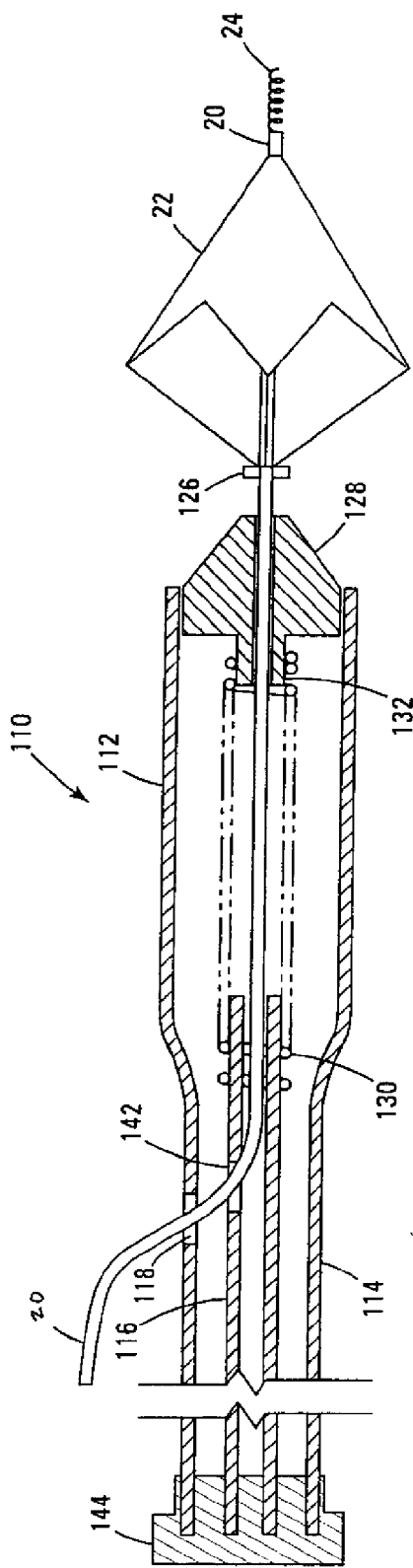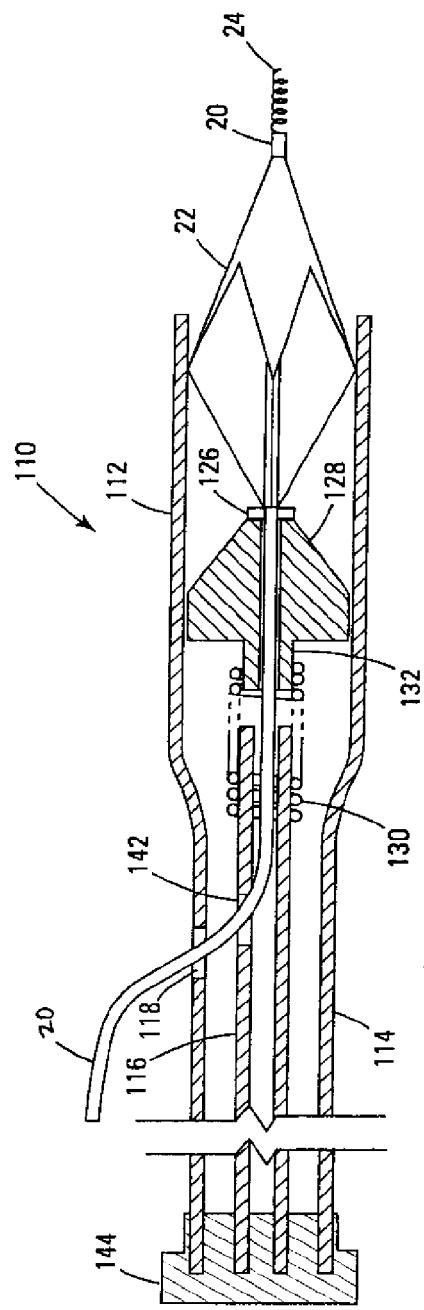

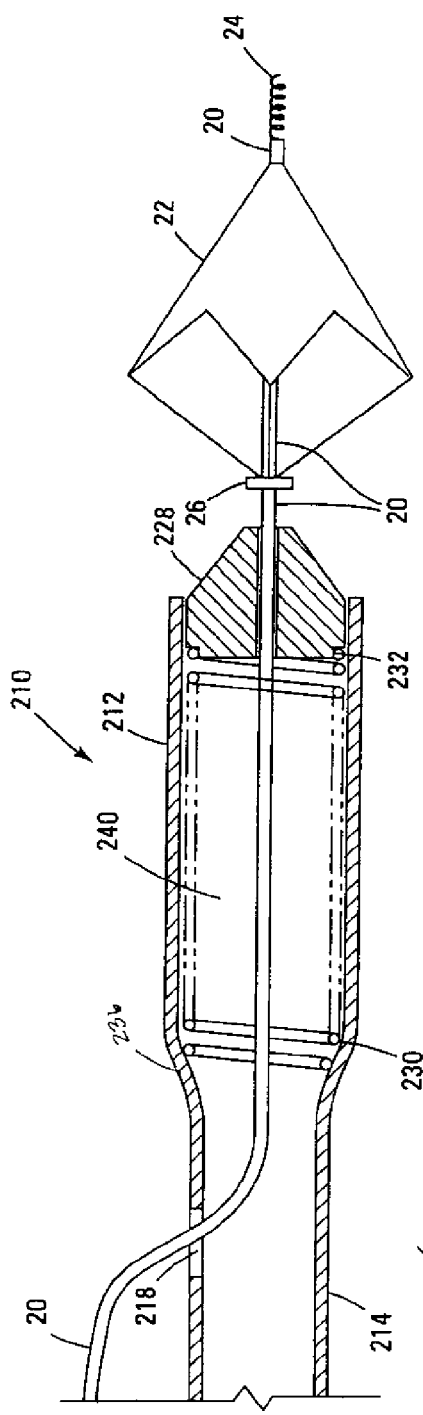
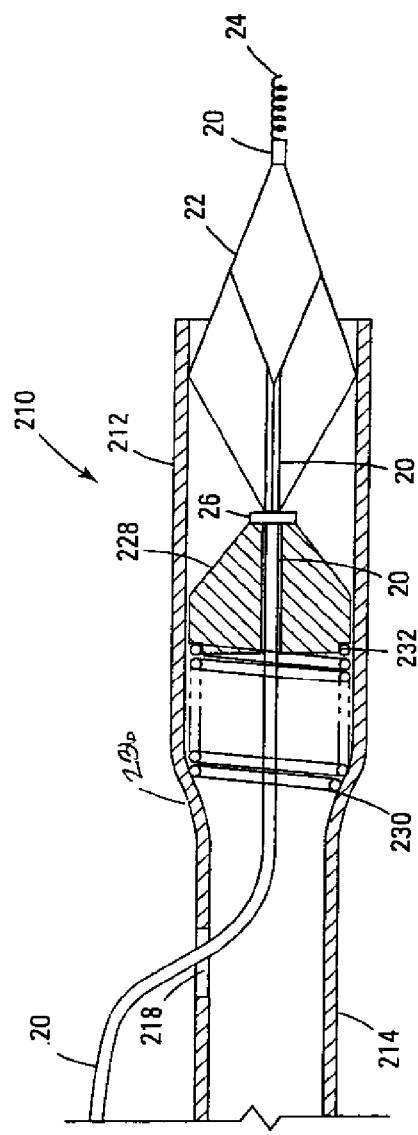

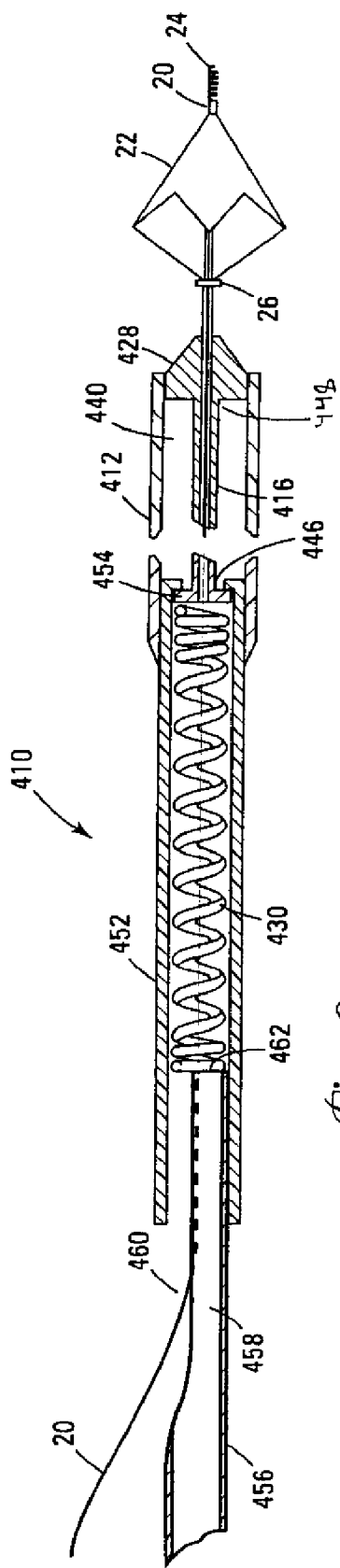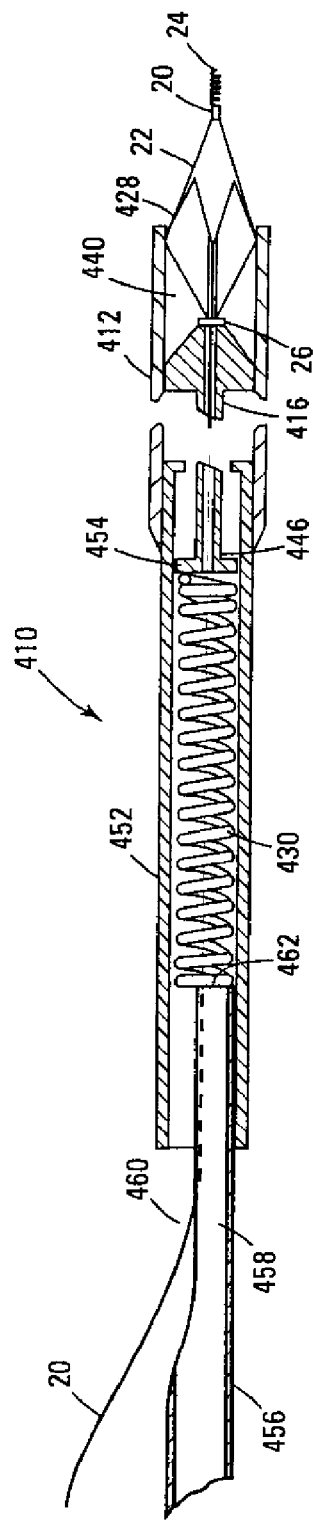

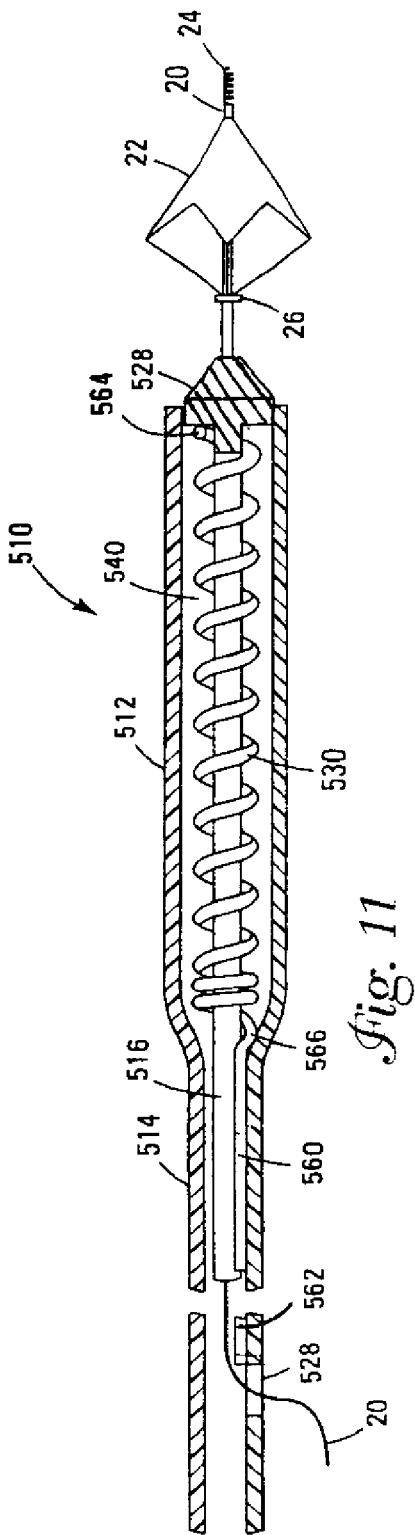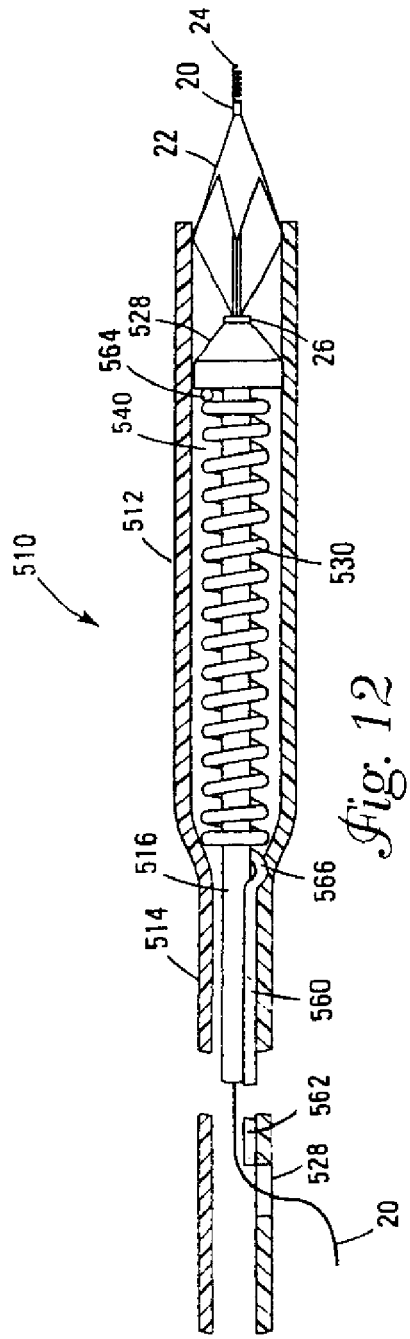
Fig. 11
Fig. 12

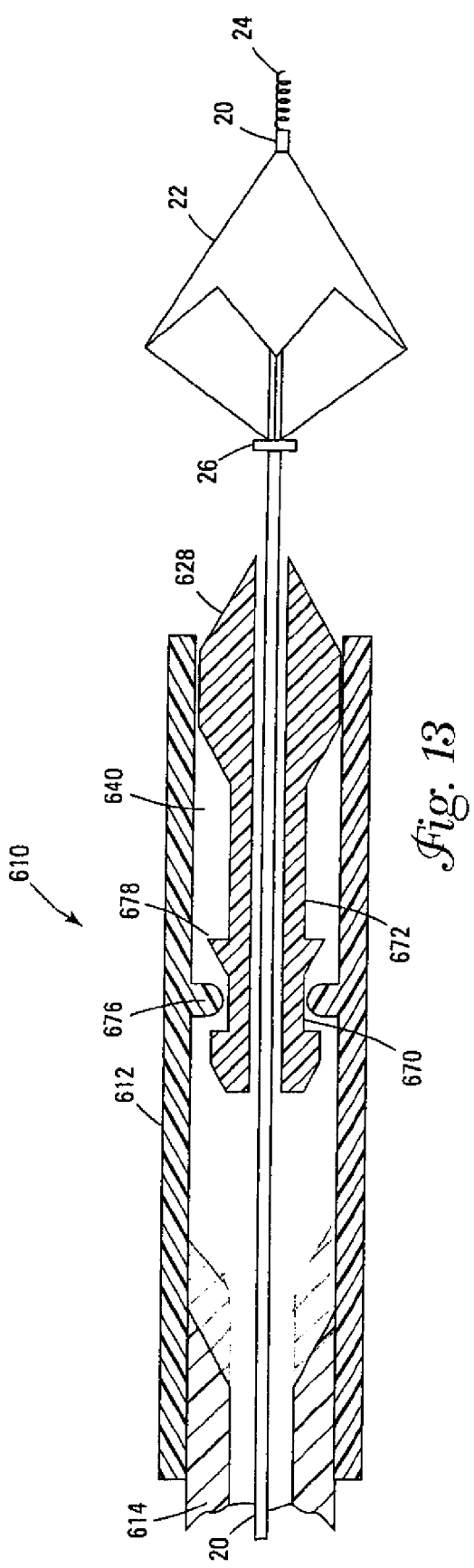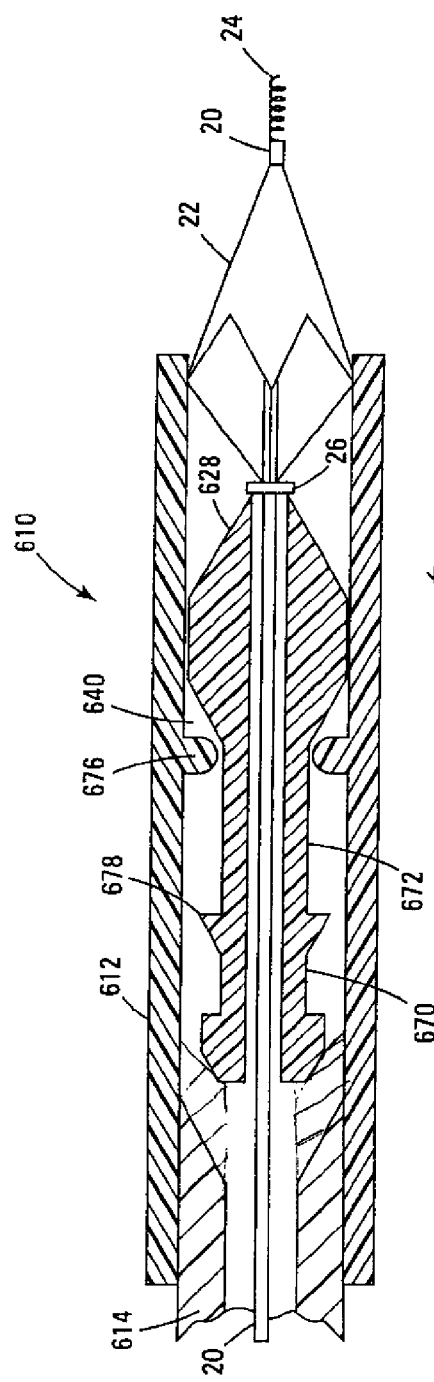

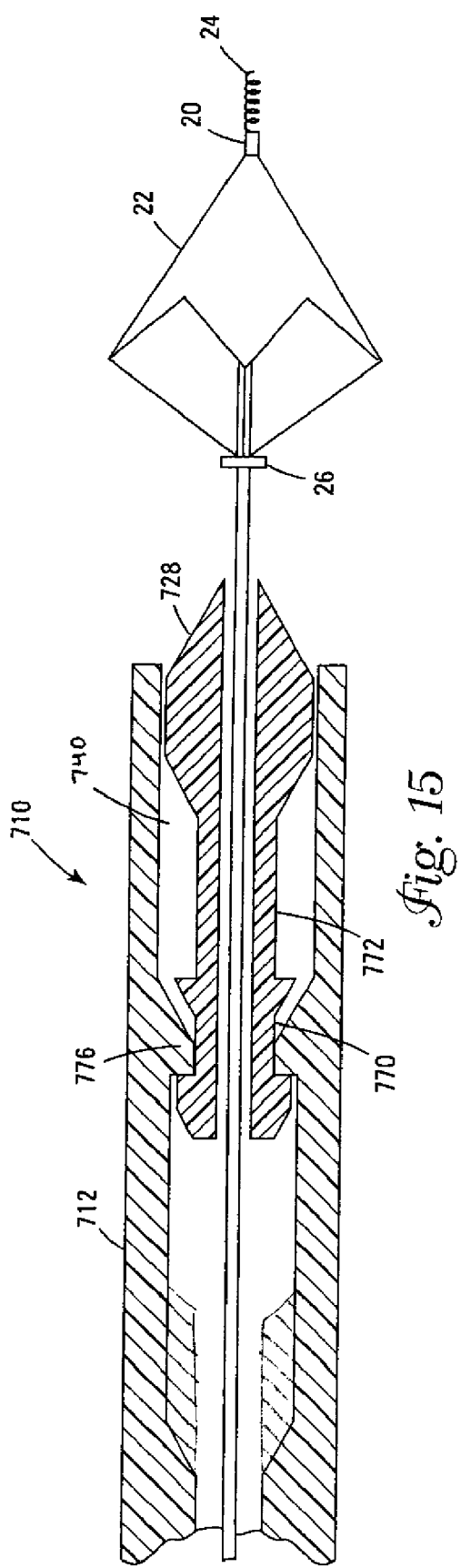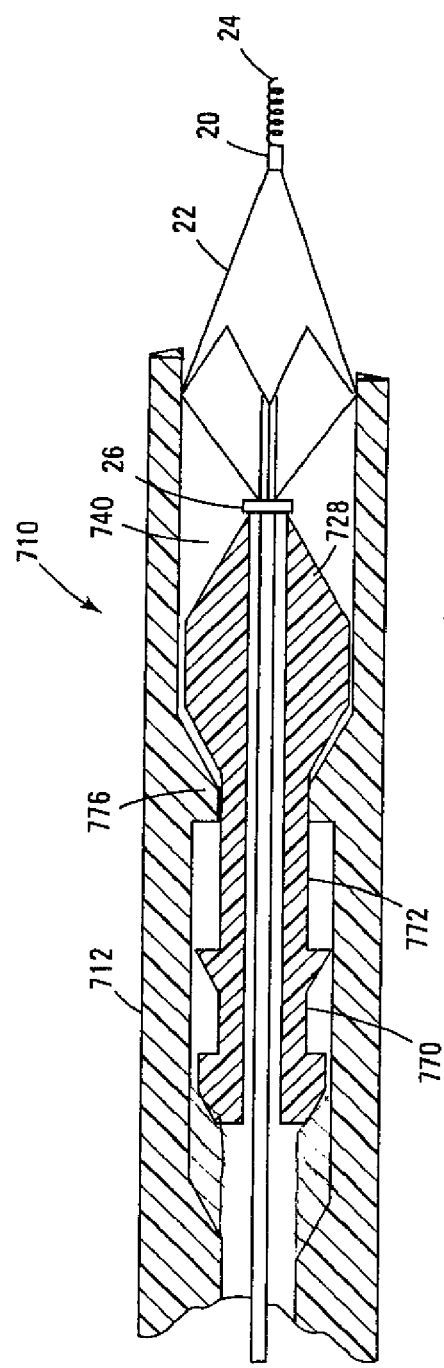

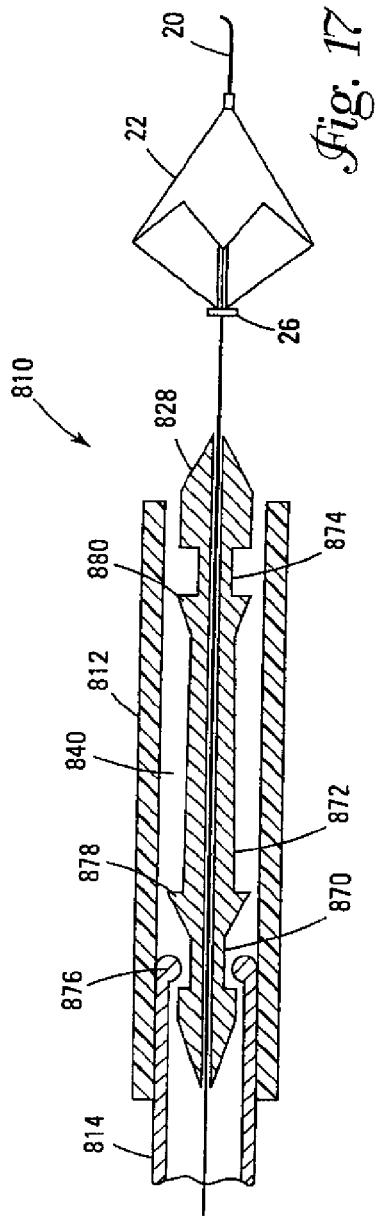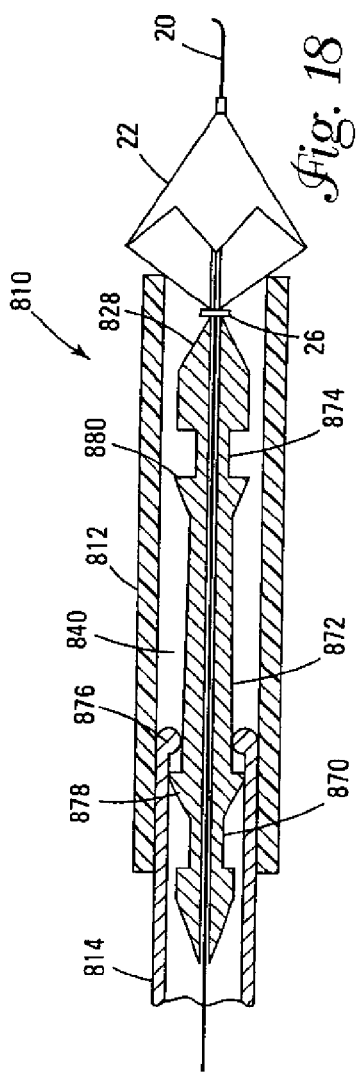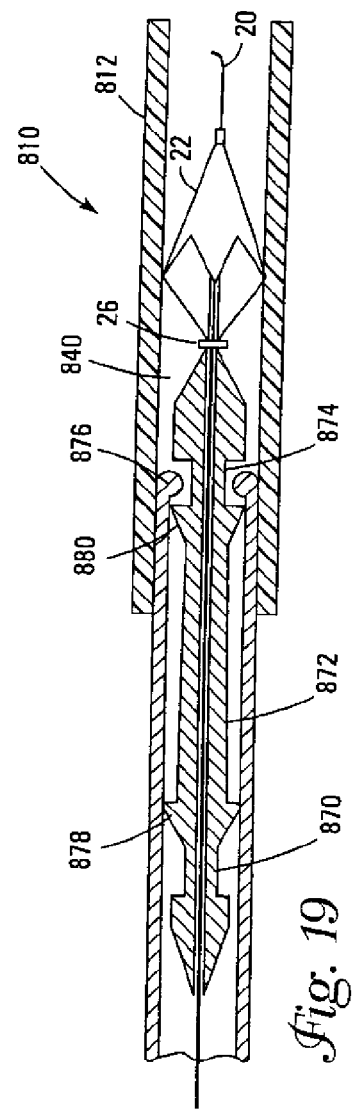

INTRAVASCULAR FILTER RETRIEVAL DEVICE HAVING AN ACTUATABLE DILATOR TIP

CROSS REFERENCE TO RELATED APPLICATION

This application is a continuation of U.S. application Ser. No. 10/083,810 filed Feb. 27, 2002, which claims the benefit of U.S. Provisional Application Ser. No. 60/272,657, filed on Mar. 1, 2001.

FIELD OF THE INVENTION

The present invention relates generally to the field of embolic protection devices. More specifically, the present invention pertains to retrieval devices for intravascular filters.

BACKGROUND OF THE INVENTION

Intravascular filters such as embolic protection filters are generally placed within a body lumen, such as an artery or vein, downstream of a site where a therapeutic device will be used. Examples of procedures employing such filters include angioplasty, atherectomy, thrombectomy and stent placement. These procedures typically involve transluminally inserting and delivering within the artery or vein, a filter wire and filter to a location distal a coronary lesion. Once in place, a therapeutic device such as an angioplasty balloon or an atherectomy catheter can be advanced to the site of the lesion to perform the procedure. During the procedure, embolic material such as plaque or thrombus become dislodged from the walls of the body lumen, and flow downstream where they are collected by the filter. After the procedure is performed, the therapeutic device and filter containing the debris, if any, can be removed from the body.

SUMMARY OF THE INVENTION

The present invention relates generally to the field of embolic protection devices. More specifically, the present invention pertains to retrieval devices for intravascular filters. In one embodiment in accordance with the present invention, a filter retrieval device includes a distal sheath and an outer shaft extending proximally therefrom. A dilator tip is biased toward the distal end of the distal sheath by a resilient member. In one particular implementation, the resilient member may include a spring coil having one or more coils helically disposed along the filter wire. In an alternative implementation, the resilient member may include a spring having one or more struts longitudinally disposed along the filter wire. In use, the filter retrieval device is advanced along the filter wire until the dilator tip contacts a proximal filter stop. The filter retrieval device is then further advanced such that the filter collapses and is contained at least in part within the distal sheath.

In a similar embodiment, a filter retrieval device comprises a distal sheath and an outer shaft extending proximally therefrom, an actuatable dilator tip, and an inner shaft disposed at least in part within the lumen formed by the distal sheath. As with the aforementioned embodiment, the dilator tip is biased toward the distal end of the distal sheath by a resilient member such as a spring coil. The inner shaft may have a length substantially similar to the length of the outer shaft. Alternatively, the inner shaft may have a length substantially shorter than the length of the outer shaft. In the latter case, an exchange port can be disposed on the outer shaft to permit single operator advancement of the filter retrieval device.

In another embodiment of the present invention, a filter retrieval device comprises a distal sheath, a shaft, and a dilator tip slidably disposable along a filter wire. The distal sheath has a reduced inner diameter portion adapted to engage a recessed surface disposed on a portion of the dilator tip. In one particular implementation, the recessed surface includes a first recessed surface disposed on a proximal portion of the dilator tip, and a second recessed surface disposed on the dilator tip distal the first recessed surface. Prior to use, the operator attaches the dilator tip to the distal sheath by engaging the reduced inner diameter portion along the first recessed surface. To retrieve the filter, the operator then advances the device along the filter wire until the distal end of the dilator tip contacts the filter stop. Once the dilator tip is attached to the filter stop, further advancement of the dilator tip causes the reduced inner diameter portion of the distal sheath to engage the second recessed surface on the dilator tip. Continued advancement of the dilator tip causes the filter to retract at least in part within the distal sheath. A third recessed surface disposed on the dilator tip distal the second recessed surface may be utilized to provide the operator with tactile feedback that the filter has been retracted into the distal sheath a sufficient distance to permit removal from the body.

BRIEF DESCRIPTION OF THE DRAWINGS

FIG. 1 is a cross-sectional view of a filter retrieval device in accordance with the present invention advanced to a distal protection filter;

FIG. 2 is a cross-sectional view of the device of FIG. 1, wherein the catheter is advanced at least in part over the filter;

FIG. 3 is a cross-sectional view of a second embodiment of a filter retrieval device in accordance with the present invention advanced to a distal protection filter;

FIG. 4 is a cross-sectional view of the device of FIG. 3, wherein the catheter is advanced at least in part over the filter;

FIG. 5 is a cross-sectional view of another embodiment of a filter retrieval device in accordance with the present invention advanced to a distal protection filter;

FIG. 6 is a cross-sectional view of the device of FIG. 5, wherein the catheter is advanced at least in part over the filter;

FIG. 9 is a cross-sectional view of a filter retrieval device in accordance with another embodiment of the present invention having a plunger assembly;

FIG. 10 is a cross-sectional view of the filter retrieval device of FIG. 9, wherein the catheter is advanced at least in part over the filter;

FIG. 11 is a cross-sectional view of a filter retrieval device in accordance with the present invention advanced to a distal protection filter;

FIG. 12 is a cross-sectional view of the device of FIG. 11, wherein the catheter is advanced at least in part over the filter;

FIG. 13 is a cross-sectional view of a filter retrieval device in accordance with the present invention employing a snap-fit mechanism;

FIG. 14 is a cross-sectional view of the filter retrieval device of FIG. 13, wherein the device is advanced at least in part over the filter;

FIG. 15 is a cross-sectional view of another embodiment of a filter retrieval device in accordance with the present invention employing a snap-fit mechanism;

FIG. 16 is a cross-sectional view of the filter retrieval device of FIG. 15, wherein the catheter is advanced at least in part over the filter;

FIG. 17 is a cross-sectional view of a filter retrieval device in accordance with yet another embodiment of the present invention, wherein the device is in a first position advanced to a distal protection filter;

FIG. 18 is a cross-sectional view of the filter retrieval device of FIG. 17, wherein the device is in a second position attached to the filter;

FIG. 19 is a cross-sectional view of the filter retrieval device of FIG. 17, wherein the device is in a third position fully advanced over the filter;

DETAILED DESCRIPTION OF THE INVENTION

Figure 7:
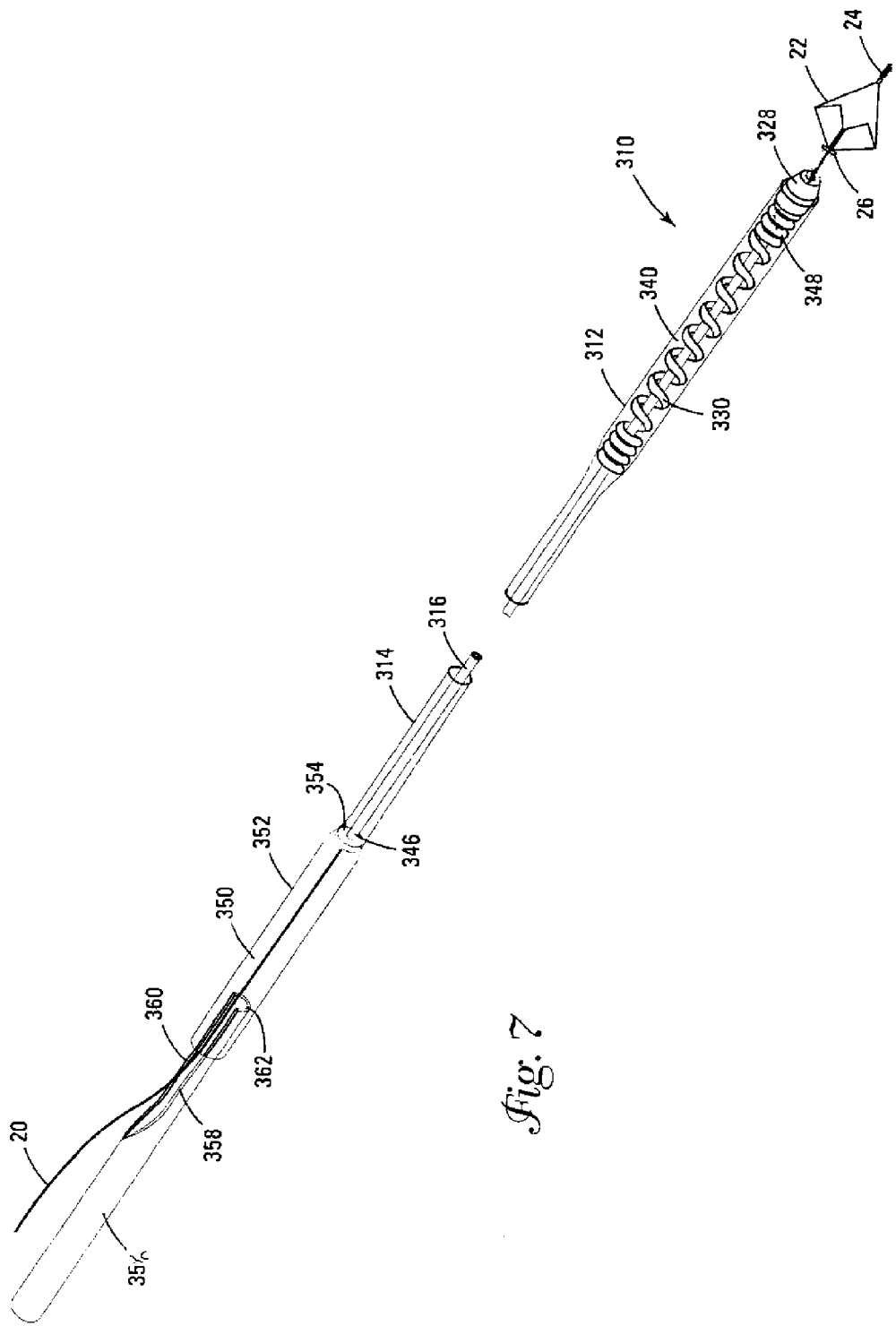
FIG. 7 is a plan view of a filter retrieval device in accordance with the present invention, wherein the device includes a plunger assembly.

Referring now to the drawings wherein like reference numerals refer to like elements throughout the several views, FIG. 1 is a cross-sectional view of a filter retrieval catheter 10 in accordance with the present invention. Filter retrieval catheter 10 includes an outer shaft 14 and a generally cylindrical distal sheath 12 extending distally thereof. Distal sheath 12 defines a lumen 40 adapted to contain an intravascular filter such as the distal protection filter 22 shown in FIG. 1, once collapsed.

As shown in FIG. 1, catheter 10 has been advanced along a filter wire 20 to filter 22 disposed at the distal end of filter wire 20. Filter wire 20 includes a distal tip 24 which can be a spring tip. A filter stop 26 is disposed on filter wire 20 proximate and proximal the filter 22. Although the particular distal tip 24 shown in FIG. 1 is substantially straight, an arcuate or "J" shaped distal tip (not shown) can be utilized to facilitate steering and tracking during advancement of filter wire 20 through the body.

Catheter 10 further includes an inner shaft 16 disposable at least in part within lumen 40 formed by distal sheath 12. Inner shaft 16 exits catheter 10 proximally at opening 18. In the particular embodiment shown in FIG. 1, inner shaft 16 has a length substantially shorter than the length of outer shaft 14 to enable single operator advancement of catheter 10 within the body.

Also disposed within distal sheath 12 is a dilator tip 28 and a spring coil 30. Dilator tip 28 has a generally circular cross section and conical-shaped distal end. Dilator tip 28 is biased at least in part out of the distal end of distal sheath 12 by spring coil 30. In the particular embodiment shown in FIG. 1, the proximal end of spring coil 30 is bonded to a portion of inner shaft 16. The distal end of spring coil 30, in turn, is bonded to dilator tip 28 at a distal bonding region 32.

In use, for example, filter 22 is positioned in a body vessel distally of a location where a therapeutic device is to be used. In an application, filter 22 can be positioned distally of a coronary lesion. A therapeutic device such as an angioplasty catheter can be advanced over filter wire 20 to the lesion. Coronary angioplasty can be performed by the angioplasty catheter and debris dislodged by the procedure can be captured in filter 22. The angioplasty catheter can then be withdrawn. Catheter 10 can then be advanced over filter wire 20 until dilator tip 28 contacts filter stop 26. Catheter 10 can then be further advanced such that spring coil 30 is compressed and dilator tip 28 is drawn into lumen 40 of distal sheath 12. Catheter 10 is further advanced until filter 22 is disposed at least in part within distal sheath 12, as shown in FIG. 2. Then catheter 10, filter wire 20, filter 22 and the collected debris can then be removed from the vessel lumen.

In an alternative embodiment to that shown in FIGS. 1-2, a filter retrieval device having an inner shaft with a length substantially similar to the length of the outer shaft may be utilized. For example, in the particular embodiment shown in FIG. 3, the proximal end of inner shaft 116 terminates at or near the proximal end of outer shaft 114. Openings 142 and 118 are provided on inner shaft 116 and outer shaft 114, respectively, to permit single operator advancement of the catheter. As with the previous embodiment, a spring coil 130 is bonded to a portion of inner shaft 116, and to bonding region 132 on dilator tip 128.

A locking hub 144 disposed at or near the proximal end of the catheter is further provided to prevent relative motion between inner shaft 116 and outer shaft 114. Locking hub 144 may be attached to the inner and outer shafts by adhesive, solder or other attachment means, or by a releasable lock mechanism (not shown).

To retrieve the filter 22, outer shaft 114 is locked to inner sheath 116 by locking hub 144. Catheter 110 is advanced to a desired site in the body proximate and proximal filter 22. The catheter is then further advanced until dilator tip 128 attaches to filter stop 26. Once attached to filter stop 26, dilator tip 128 is retracted proximally, causing filter 22 to collapse at least in part within lumen 140 formed by distal sheath 112, as shown in FIG. 4.

FIG. 5 is a cross-sectional view of another embodiment of a filter retrieval device in accordance with the present invention. Catheter 210 includes a generally cylindrical distal sheath 212 and an outer shaft 214 extending proximally therefrom. Outer shaft 214 includes a side opening 218 to enable single operator advancement of catheter 210 within the body. A dilator tip 228 is disposable at least in part within the lumen 240 formed by distal sheath 212.

As shown in FIG. 5, Dilator tip 228 is biased at least in part distally from distal sheath 212 by a spring coil 230. The distal end of spring coil 230 can be bonded to dilator tip 228 at a dilator bonding region 232. A tapered portion 236 disposed on the catheter prevents spring coil 230 from retracting proximally from distal sheath 212, when actuated.

Catheter 210 is used in a manner similar to that of catheters 10 and 110. For example, as illustrated in FIG. 6, filter 22 can be collapsed and drawn into distal sheath 212 in a manner similar to that shown and described with respect to FIGS. 2 and 4.

FIG. 7 is a plan view of another exemplary embodiment of the present invention employing a plunger assembly. Catheter 310 includes a distal sheath 312 and an outer shaft 314 extending proximally therefrom. A dilator tip 328 and spring coil 330 are disposed within the distal sheath 312, similar to the embodiment shown in FIGS. 5-6.

An inner shaft 316 having a proximal end 346 and a distal end 348 is disposed within outer shaft 314 and distal sheath 312. The distal end 348 of inner shaft 316 may be attached to the proximal end of dilator tip 328 by adhesive or other attachment means.

Catheter 310 further includes a plunger assembly comprising a tubular member 352 defining a lumen 350, and a plunger 354 formed by enlarged diameter portion on the proximal end 346 of inner shaft 316. Plunger 354 is adapted to slide along filter wire 20 within lumen 350 formed by tubular member 352. A shaft 356 extending proximally from tubular member 352 is further disposed in part within lumen 350. A distal section 358 of shaft 356 is crimped in a smiley-face configuration to permit the filter wire 20 to exit catheter 310 through opening 360, and to act as a proximal stop for plunger 354. The proximal end of outer shaft 314, which extends proximally into lumen 350 formed by tubular member 352, is adapted to act as a distal stop for plunger 354.

Figure 8:
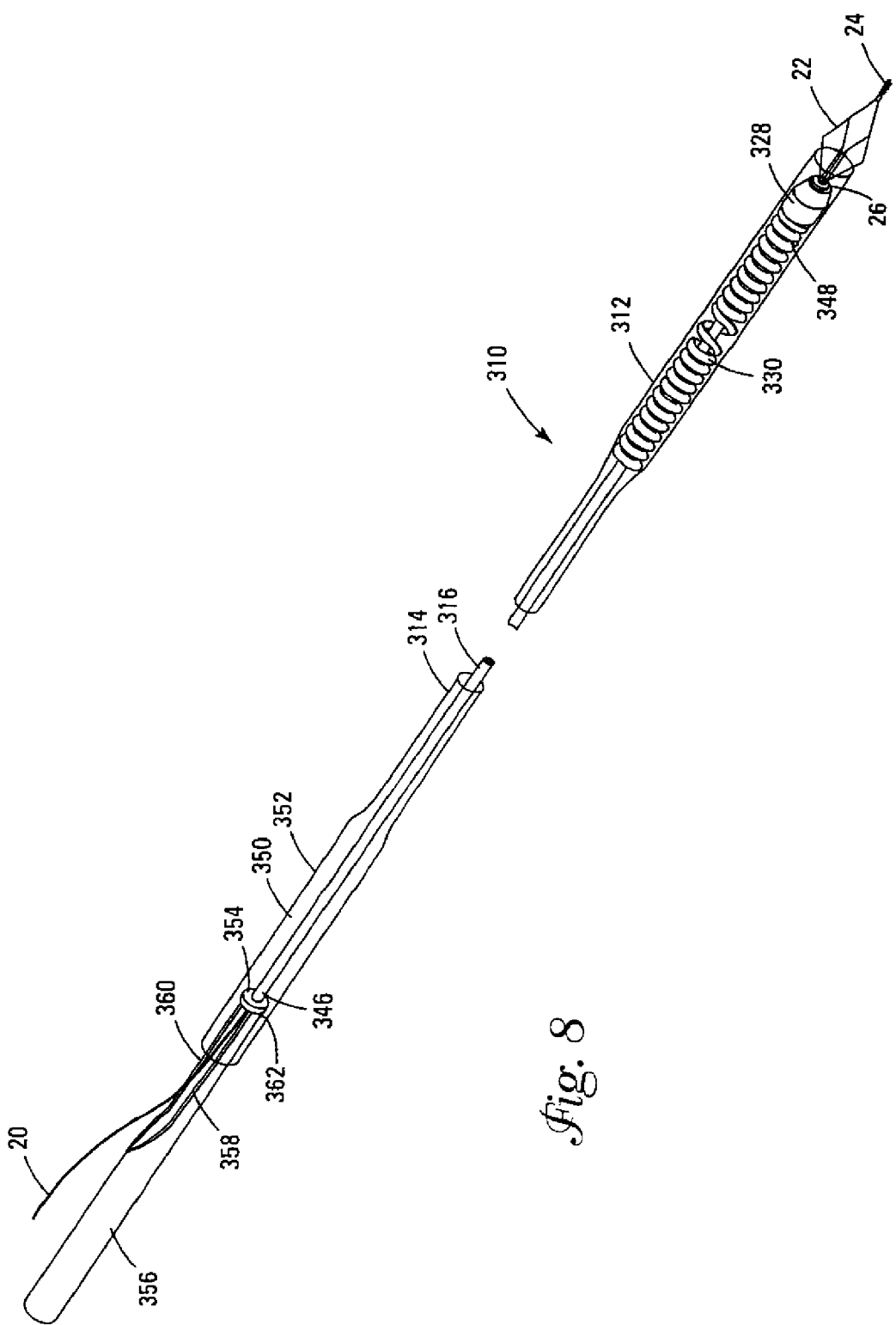
FIG. 8 is a plan view of the filter retrieval device of FIG. 7, wherein the device is advanced at least in part over the filter.

In use, spring coil 330 biases the dilator tip 328 at least in pan distally from distal sheath 312. To retrieve the filter, catheter 310 is advanced to a point along the filter wire 20 proximate and proximal filter stop 26. Catheter 310 is further advanced until dilator tip 328 attaches to filter stop 26. Once attached, filter wire 20 is retracted proximally, causing plunger 354 to slide proximally within tubular member 352, and filter 22 to collapse at least in part within distal sheath 312, as shown in FIG. 8. The crimped distal end 362 of shaft 356 acts as a proximal stop for plunger 354. When plunger 354 abuts distal end 362, the operator is prevented from retracting filter 22 further into distal sheath 312, thus providing the operator with tactile feedback that filter 22 is collapsed within distal sheath 312.

FIG. 9 illustrates another exemplary embodiment in accordance with the present invention. In the particular embodiment shown in FIG. 9, spring coil 430 is disposed within tubular member 452 proximal an inner shaft 416. Inner shaft 416 has a proximal end 446 and a distal end 448. An enlarged diameter portion disposed on the proximal end 446 of inner shaft 416 forms a plunger 454. The distal end 448 of inner shaft 416 is attached to dilator tip 428.

Spring coil 430 is adapted to bias the dilator tip 428 distally from distal sheath 412. As with the embodiment illustrated in FIGS. 8-9, the crimped distal end 462 of shaft 456 is adapted to hold spring coil 430 in partial compression, and to prevent spring coil 430 from retracting proximally.

To retrieve the filter, catheter 410 is advanced along the filter wire 20 until dilator tip 428 contacts filter stop 26. Further advancement of catheter 410 causes the filter 22 to collapse within the lumen 440 of distal sheath 412, as shown in FIG. 10. Then the catheter containing filter wire 20, filter 22 and the debris can be removed from the body.

FIGS. 11 and 12 are cross-sectional views of a filter retrieval device in accordance with yet another embodiment of the present invention. Catheter 510 includes a cylindrical distal sheath 512 coupled to an outer shaft 514 distally thereof. Disposable at least in part within lumen 540 of distal sheath 512 is a dilator tip 528 similar to that depicted in FIGS. 9-10. Dilator tip 528 is biased at least in part distally from distal sheath 512 by a spring coil 530.

Spring coil 530 is formed by a portion of a wire 560 that has a proximal end 562 and a distal end 564. The proximal end 562 of wire 560 is attached to outer shaft 514 at or near opening 518. Wire 560 is substantially straight from proximal end 562 to point 566, and is helically disposed about inner shaft 516 from point 566 to distal end 564.

In use, when catheter 530 is advanced distally, dilator tip 528 attaches to filter stop 26. Further advancement of the catheter causes filter 22 to collapse and retract at least in part into the distal sheath 512, as shown in FIG. 12.

Although the particular embodiments depicted in FIGS. 1-12 utilize a helically disposed spring coil to bias the dilator tip distally from the distal sheath, other configurations are possible without deviating from the scope of the invention. For example, a spring having one or more struts disposed longitudinally along the axis formed by the filter wire may be used to bias the dilator tip distally from the distal sheath. In yet another example, the spring may comprise an accordion-shaped polymeric tube adapted to bias the dilator tip distally from the distal sheath.

It is also to be understood that several different materials may be utilized to form the resilient members without deviating from the scope of the present invention. For example, the spring coil may be comprised of 304 or 316 grade stainless steel, or may be comprised of a polymeric material such as polyethylene (PE), polypropylene (PP), polyvinylchloride (PVC) or polytetrafluoroethylene (PTFE).

FIG. 13 illustrates yet another exemplary embodiment of the present invention utilizing a snap-fit mechanism to retrieve the filter. Filter retrieval catheter 610 includes a distal sheath 612 coupled to a shaft 614 extending proximally therefrom. Distal sheath 612 defines a lumen 640 adapted to carry a filter such as a distal protection filter, once collapsed.

Disposable at least in part within lumen 640 is a dilator tip 628. Dilator tip 628 is comprised of a substantially hard material, and includes several recessed surfaces adapted to permit relative motion between the dilator tip 628 and the distal sheath 612. In the particular embodiment shown in FIG. 13, dilator tip 628 includes a first recessed surface 670 disposed on a proximal portion of dilator tip 628, and a second recessed surface 672 disposed distally the first recessed surface 670, The first recessed surface 670 and second recessed surface 672 are adapted to permit a reduced inner diameter portion 676 disposed on distal sheath 612 to slide thereon.

The length of the second recessed surface can be varied depending on the actuation length desired. In an application, the length of the second recessed surface can be pre-determined to provide a sufficient actuation length to permit the filter to completely collapse within the distal sheath. This pre-determined length provides the operator with feedback on the location of the filter within the distal sheath, thus obviating the need to resort to more traditional fluoroscopic imaging techniques.

To retrieve the filter, dilator tip 628 is first attached to the distal sheath 612 prior to insertion of the device into the body. In a first position shown in FIG. 13, catheter 610 is inserted into the patient and advanced to the site of the filter to be retrieved. A barb 678 disposed on dilator tip 628 distal the first recessed surface 670 prevents dilator tip 628 from sliding relative to distal sheath 612 during delivery. Once catheter 610 has been advanced to the site, and the distal end of dilator tip 628 abuts filter stop 26, continued retraction of filter wire 20 and/or advancement of the catheter causes the reduced inner diameter portion 674 on the distal sheath 612 to overcome the frictional force exerted by barb 678. When this occurs, barb 678 displaces distally, allowing reduced inner diameter portion 676 to engage the second recessed surface 672. Continued retraction of reduced inner diameter portion 676 along the second recessed surface 672 draws filter 22 into delivery sheath 612, as shown in FIG. 14. Then the catheter containing the filer wire 20, collapsed filter 22 and collected debris can be withdrawn from the body.

FIG. 15 is a cross-sectional view of another embodiment in accordance with the present invention. Similar to the embodiment illustrated in FIGS. 13-14, catheter 710 includes a distal sheath 712 coupled to a shaft 714 (not shown) extending proximally therefrom. Distal sheath 712 defines a lumen 740 adapted to carry a filter such as a distal protection filter, once collapsed.

In the particular embodiment shown in FIG. 15, distal sheath 712 has a reduced inner diameter portion 776 which is adapted to slidably engage the first recessed surface 770 and second recessed surface 772 on dilator tip 728.

In use, catheter 710 operates in a manner similar to that of catheter 610. For example, as illustrated in FIG. 16, filter 22 can be collapsed and drawn into distal sheath 712 in a manner similar to that shown and described with respect to FIG. 14.

In a similar embodiment to that shown in FIGS. 13-16, a filter retrieval device having an actuatable dilator tip further comprises a third recessed surface disposed on the dilator tip to provide the operator with tactile feedback that the filter is fully drawn into the catheter. As illustrated in FIG. 17, a filter retrieval catheter 810 having an actuatable dilator tip includes a distal sheath 812 coupled to a shaft 814 distally thereof, and a dilator tip 828 slidably disposable along a filter wire 20.

Dilator tip 828 includes a first recessed surface 870 disposed on a proximal portion thereof, a second recessed surface 872 disposed distally the first recessed surface 870, and a third recessed surface 874 disposed distally the second recessed surface 872. In an application, the length of the second recessed surface 872 can be pre-determined to provide a sufficient actuation length to permit the filter to completely collapse within distal sheath 812.

To retrieve the filter, dilator tip 828 is attached to the distal sheath 812 and inserted into the patient. In a first position shown in FIG. 17, catheter 810 is advanced to a location proximate and proximal a filter 22. A barb 878 disposed on dilator tip 828 distal the first recessed surface 870 prevents dilator tip 828 from sliding relative to distal sheath 812 during delivery. Once catheter 810 has been advanced to the site, and the distal end of dilator tip 828 abuts filter stop 26, continued retraction of filter wire 20 and/or advancement of the catheter causes the reduced inner diameter portion 876 on distal sheath 812 to overcome the frictional force exerted by barb 878. Continued retraction of the reduced inner diameter portion 876 in the proximal direction along the second recessed surface 872 draws filter 22 into delivery sheath 812, as shown in FIG. 18. A second barb 880 disposed distally of the second recessed surface 872 is then engaged. When a sufficient force is exerted on the second barb 880, barb 880 displaces, allowing reduced inner diameter portion 876 to engage the third recessed surface 874 as shown in FIG. 19. When the third recessed surface 874 is engaged, continued retraction of dilator tip 828 is prevented, thus informing the operator that filter 22 has been fully encapsulated within distal sheath 812.

Figure 20:
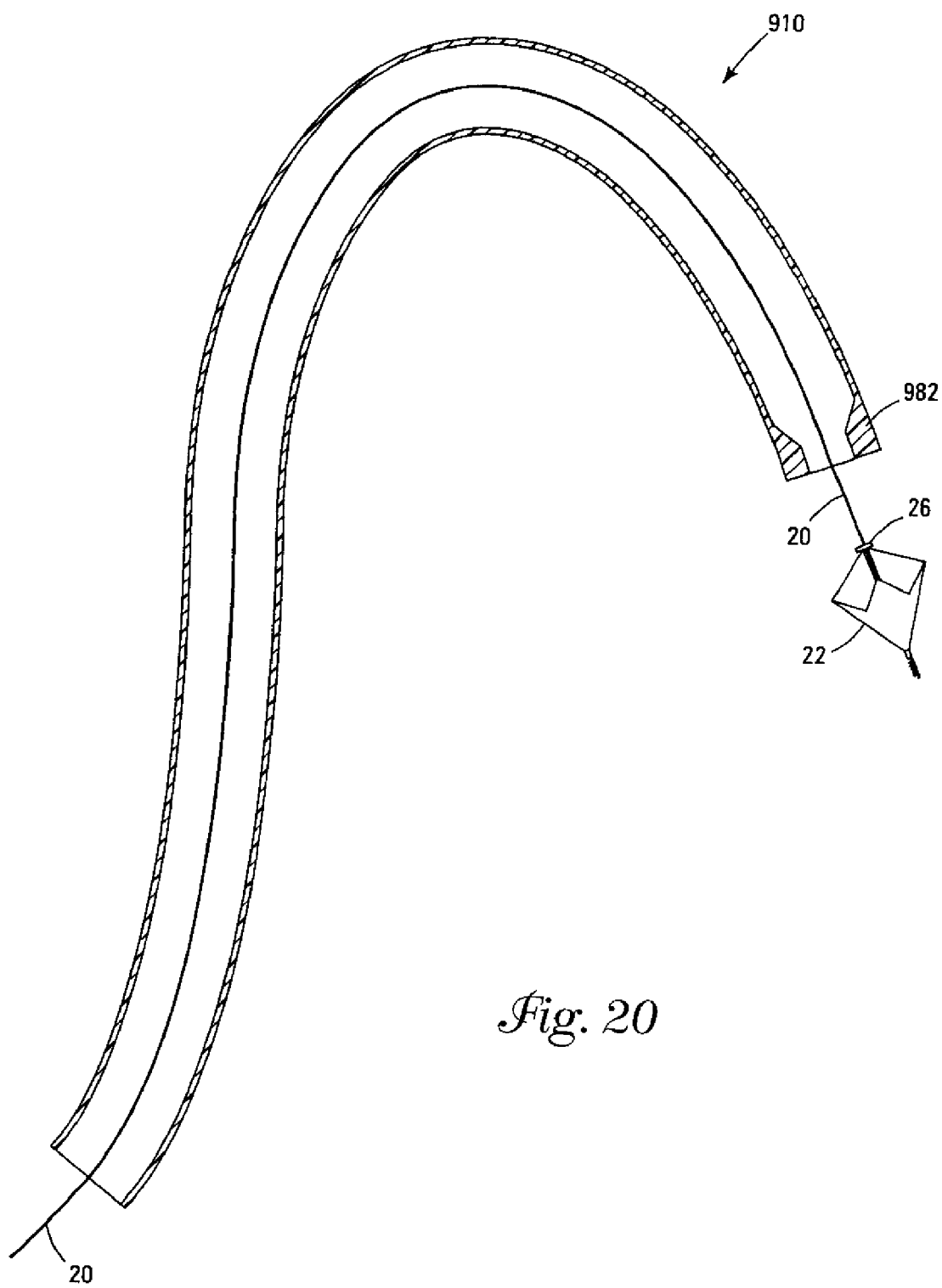
FIG. 20 is a cross-sectional view of a guide catheter, filter wire and distal protection filter disposed within a body lumen.

Referring now to FIGS. 20-27, methods for retrieving an intravascular filter from a body lumen will now be described. As shown in FIG. 20, a guide catheter 910 having a flared distal end 982 is inserted into the lumen of a patient. A guidewire 20 is inserted through the guide catheter, and is advanced to a desired site within the patient. An intravascular filter 22 such as a distal protection filter is then advanced along guidewire 20 and placed at or near the distal end thereof. In an application, filter 22 is advanced to a location distal a lesion to collect debris dislodged during a therapeutic procedure such as an angioplasty or atherectomy.

Figure 21:
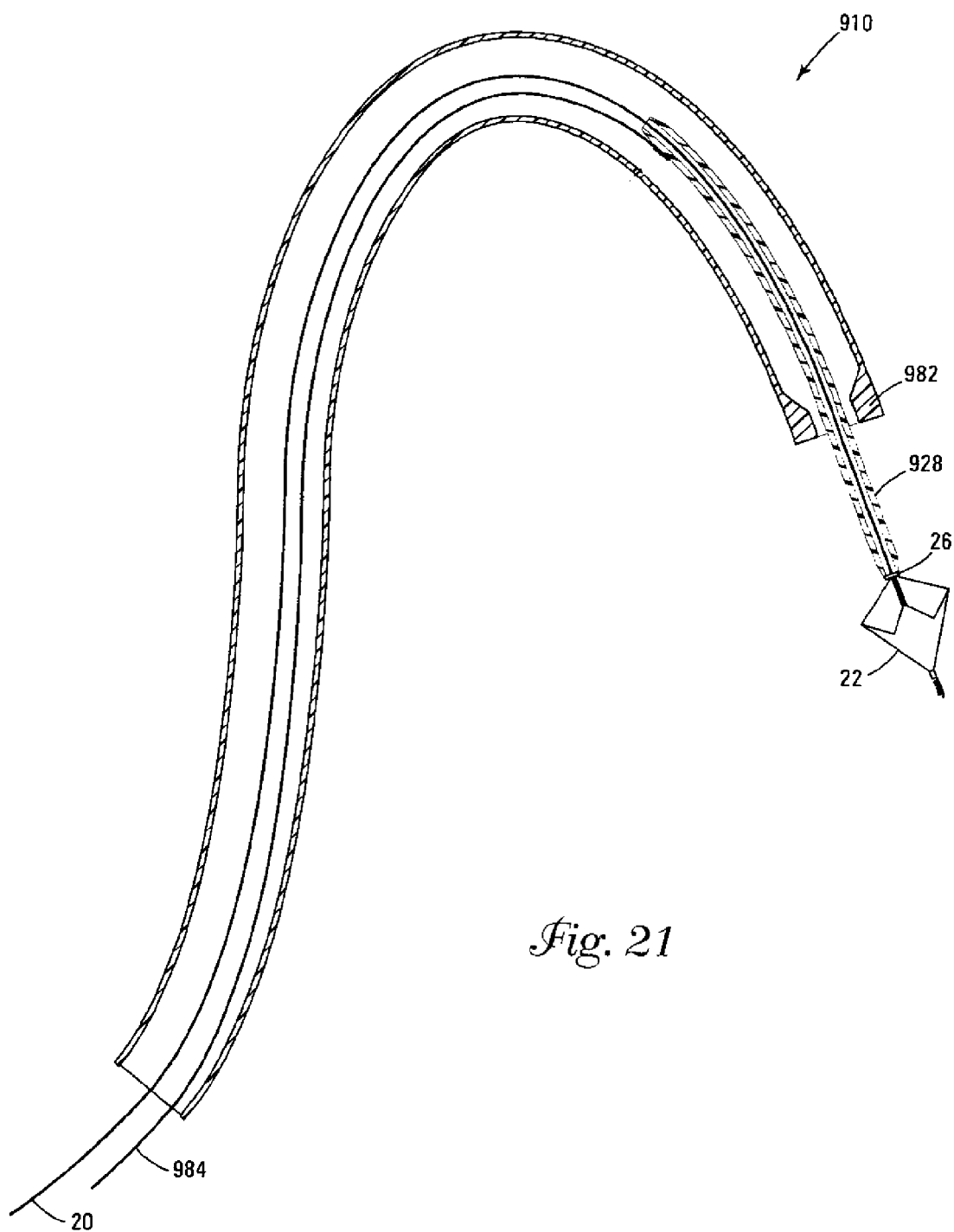
FIG. 21 is a cross-sectional view illustrating a second step of advancing and attaching a dilator to the filter.
Figure 22:
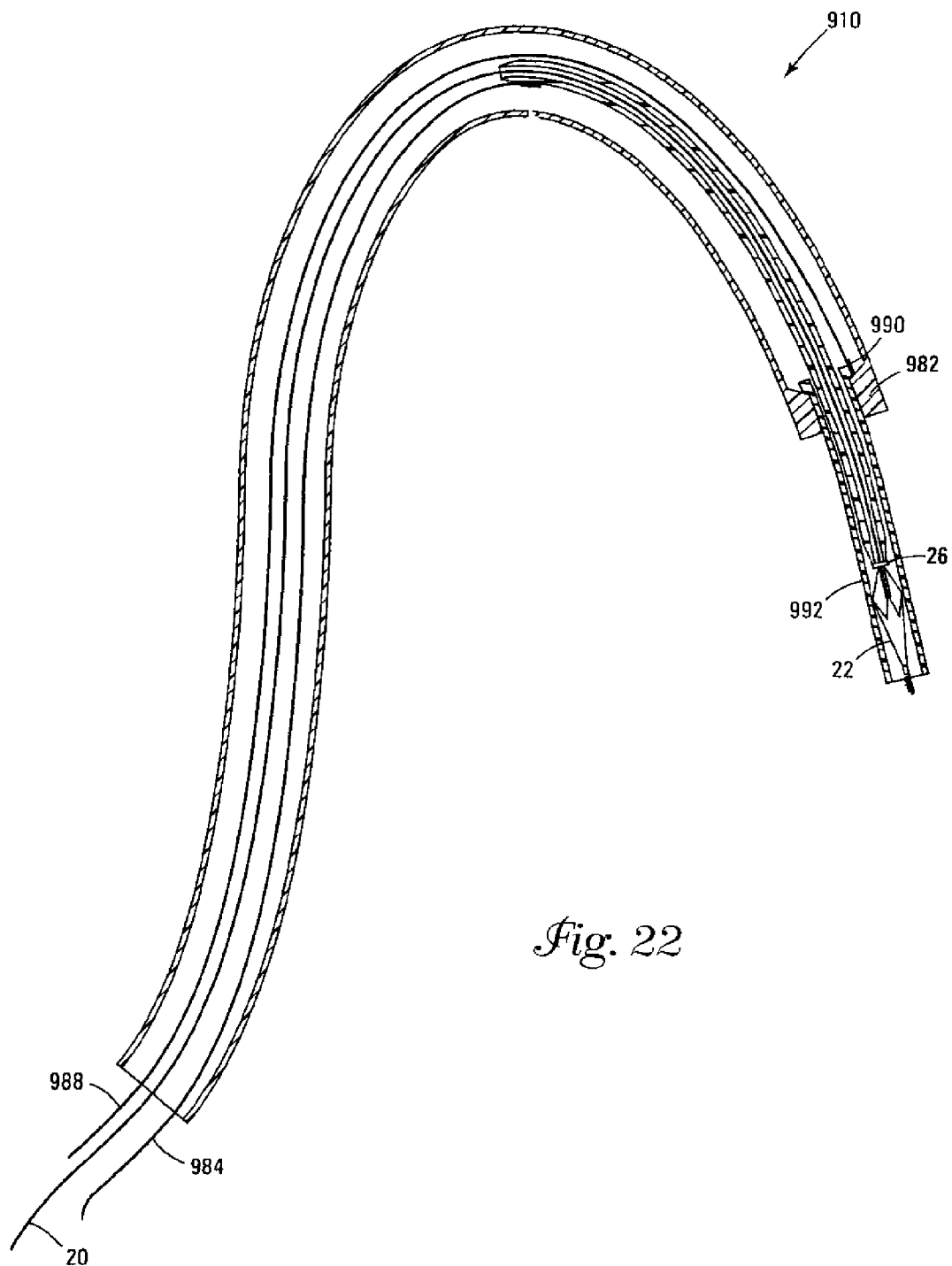
FIG. 22 is a cross-sectional view illustrating a third step of advancing an outer sheath along the guidewire and dilator and collapsing the filter therein.

To retrieve filter 22 from the body lumen, a dilator tip 928 is advanced by means of a pushing member 984 along filter wire 20 through guide catheter 910 to a point proximate and proximal filter 22. As shown in FIG. 21, the physician then further advances dilator tip 928 until it attaches to filter stop 26. Once dilator tip 928 is attached to filter stop 26, an outer sheath 992 is advanced along filter wire 20 and dilator tip 928 over filter 22, causing the filter to collapse within the outer sheath as shown in FIG. 22. Then, the dilator tip 928, filter wire 20, filter 22 and collected debris can be removed from the body.

Figure 23:
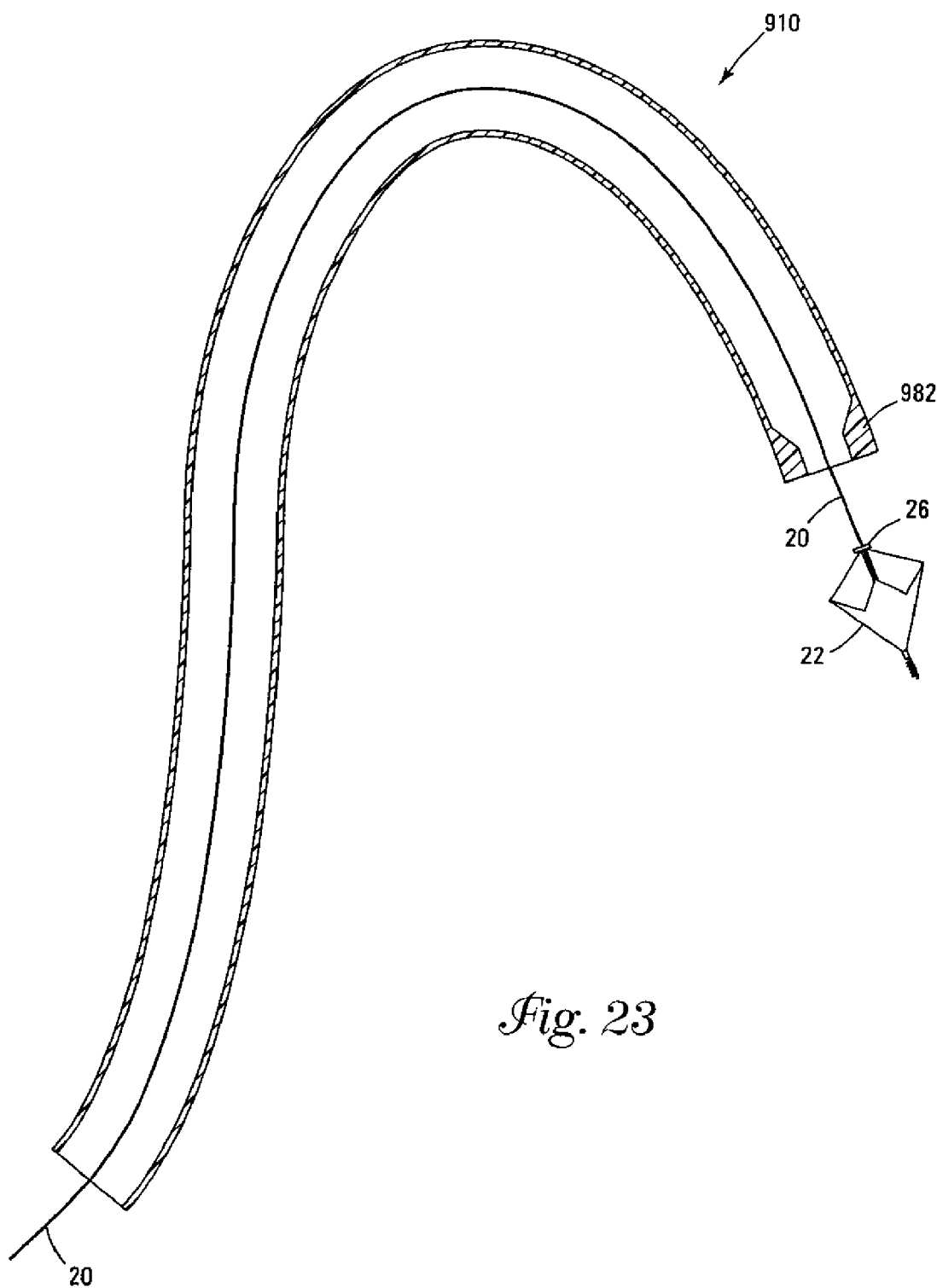
FIG. 23 is a cross-sectional view of guide catheter, filter wire and distal protection filter disposed within a body lumen.

FIGS. 23-27 illustrate an alternative method for retrieving an intravascular filter in accordance with the present invention wherein a second guidewire is placed within the body. As shown in FIG. 23, a guidewire is inserted into guide catheter 910, and is advanced to a desired location within the body where the procedure is to be performed. Disposed at or near the distal end of guidewire 20 is a filter 22.

Retrieval of the filter 22 from the body lumen proceeds in a manner similar to that illustrated in FIGS. 20-22. A dilator tip 928 is advanced along guidewire 20 by means of a pushing member 984 to a point proximate and proximal filter stop 26. Continued advancement causes the dilator tip 928 to attach to filter stop 26.

Figure 24:
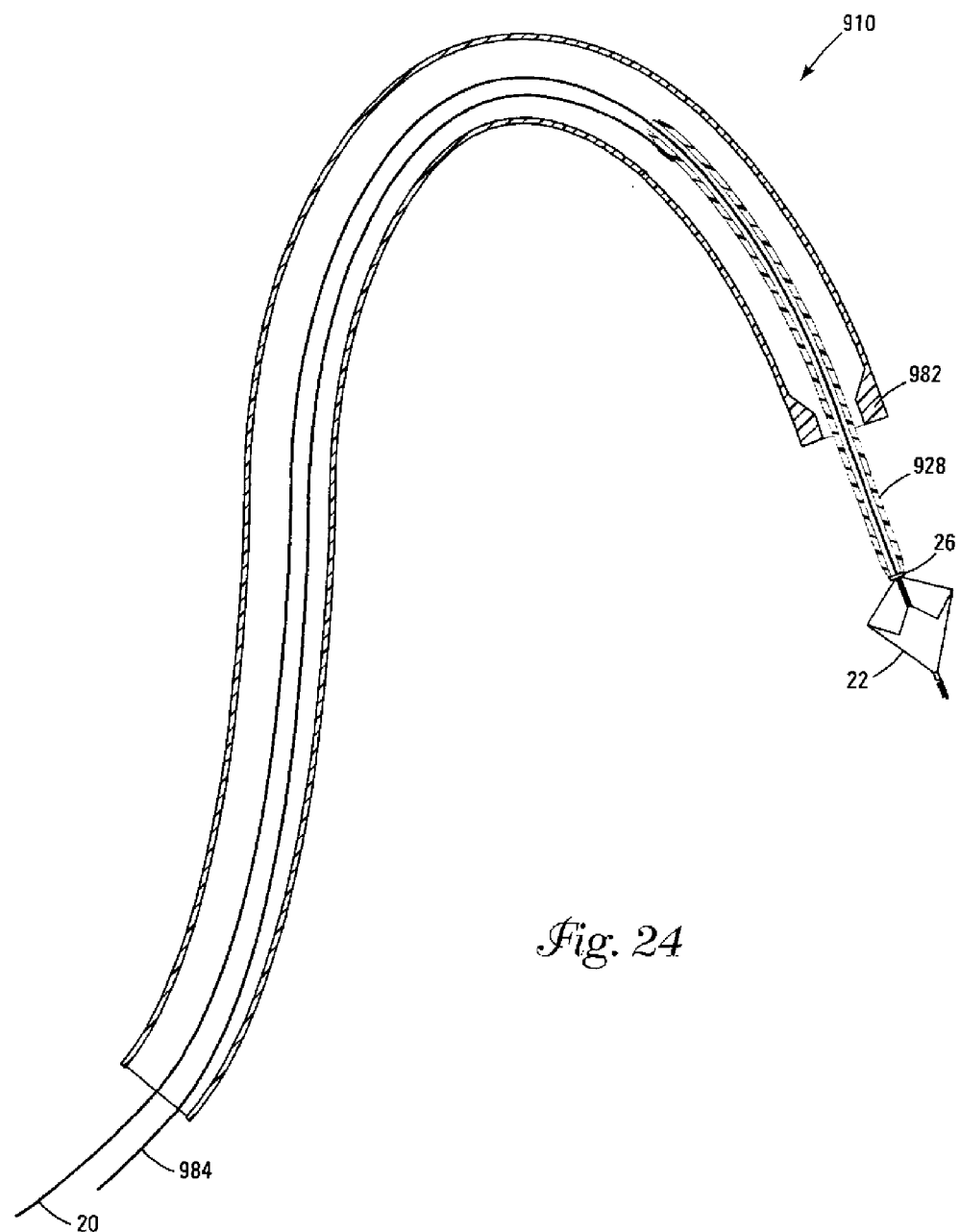
FIG. 24 is a cross-sectional view illustrating a second step of advancing and attaching a dilator to the filter.
Figure 25:
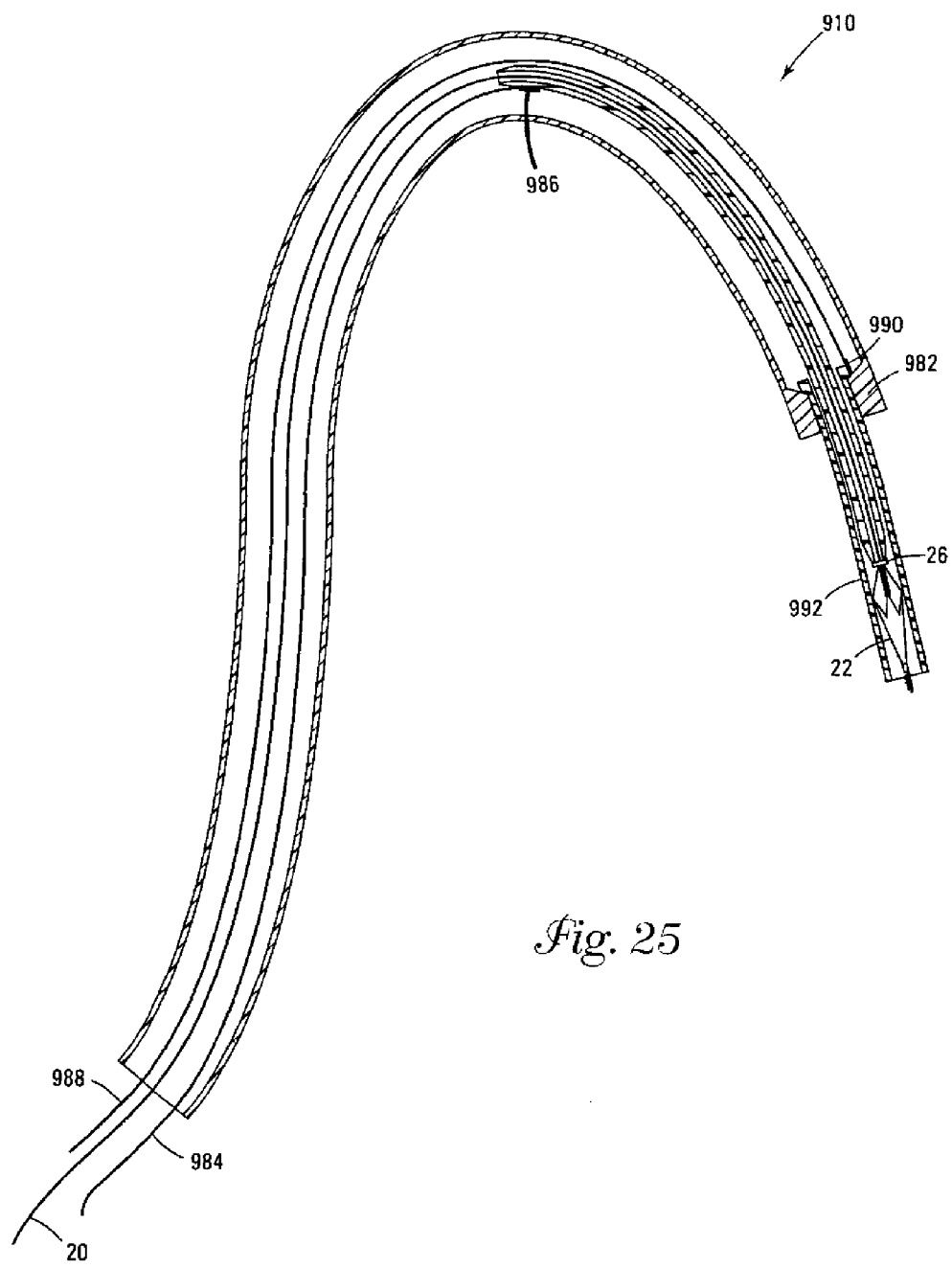
FIG. 25 is a cross-sectional view illustrating a third step of advancing an outer sheath along the guidewire and dilator and collapsing the filter therein.

As shown in FIG. 24, once dilator tip 928 is attached to the filter stop 26, an outer sheath 992 is advanced along guidewire 20 to a point distal the proximal end of filter 22, causing the filter to collapse in part within the outer sheath. The flanged portion 982 disposed on the distal end of guide catheter 910 is adapted to prevent the proximal end of outer sheath 992 from exiting the guide catheter 910 distally.

Outer sheath 992 defines a lumen adapted to carry filter 22 in a collapsed state. A marking band (not shown) disposed about a distal portion of outer sheath 992 permits the operator to fluoroscopically judge the location of the outer sheath within the body.

Figure 26:
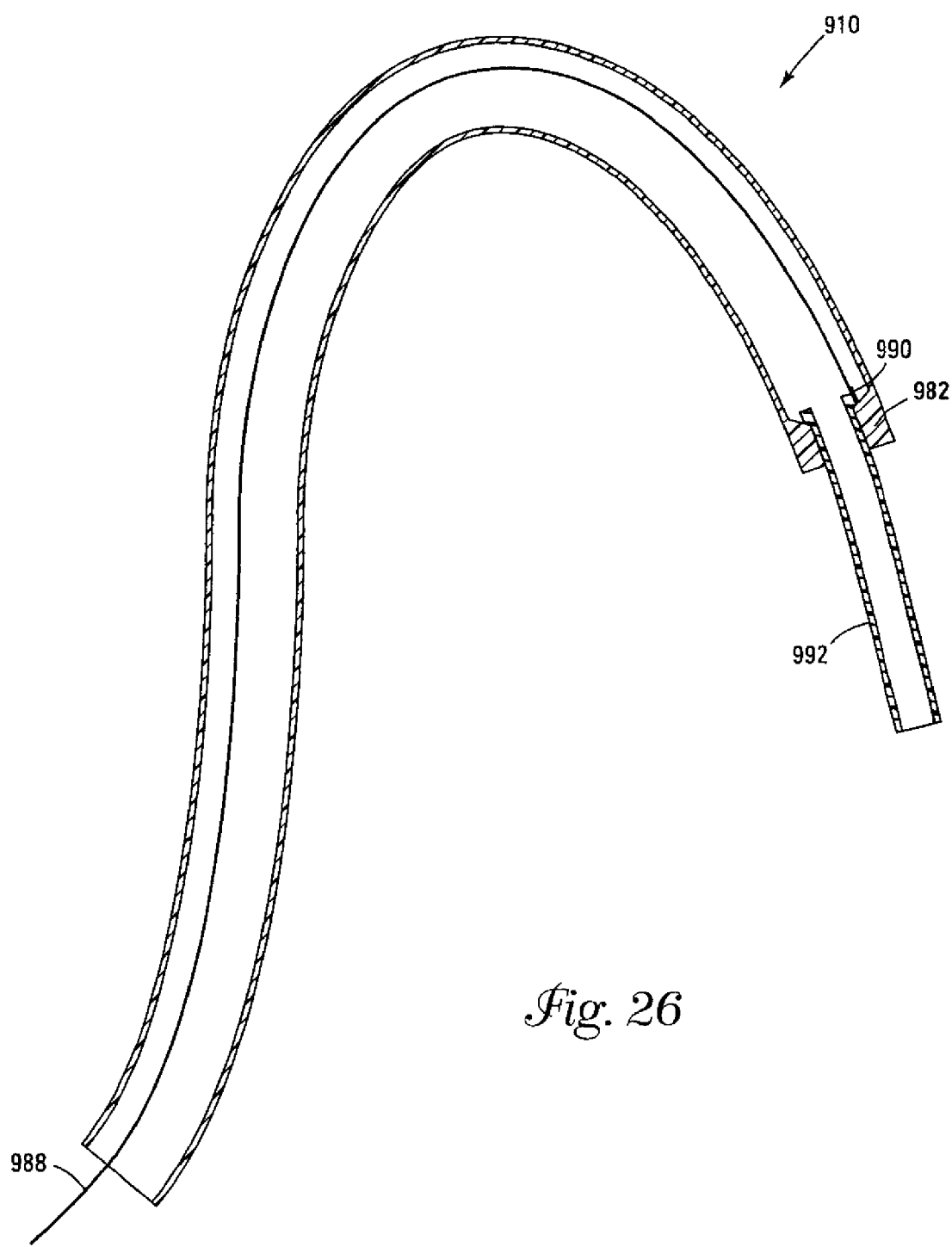
FIG. 26 is a cross-sectional view illustrating a fourth step of removing the dilator, guidewire and collapsed filter from the body.
Figure 27:
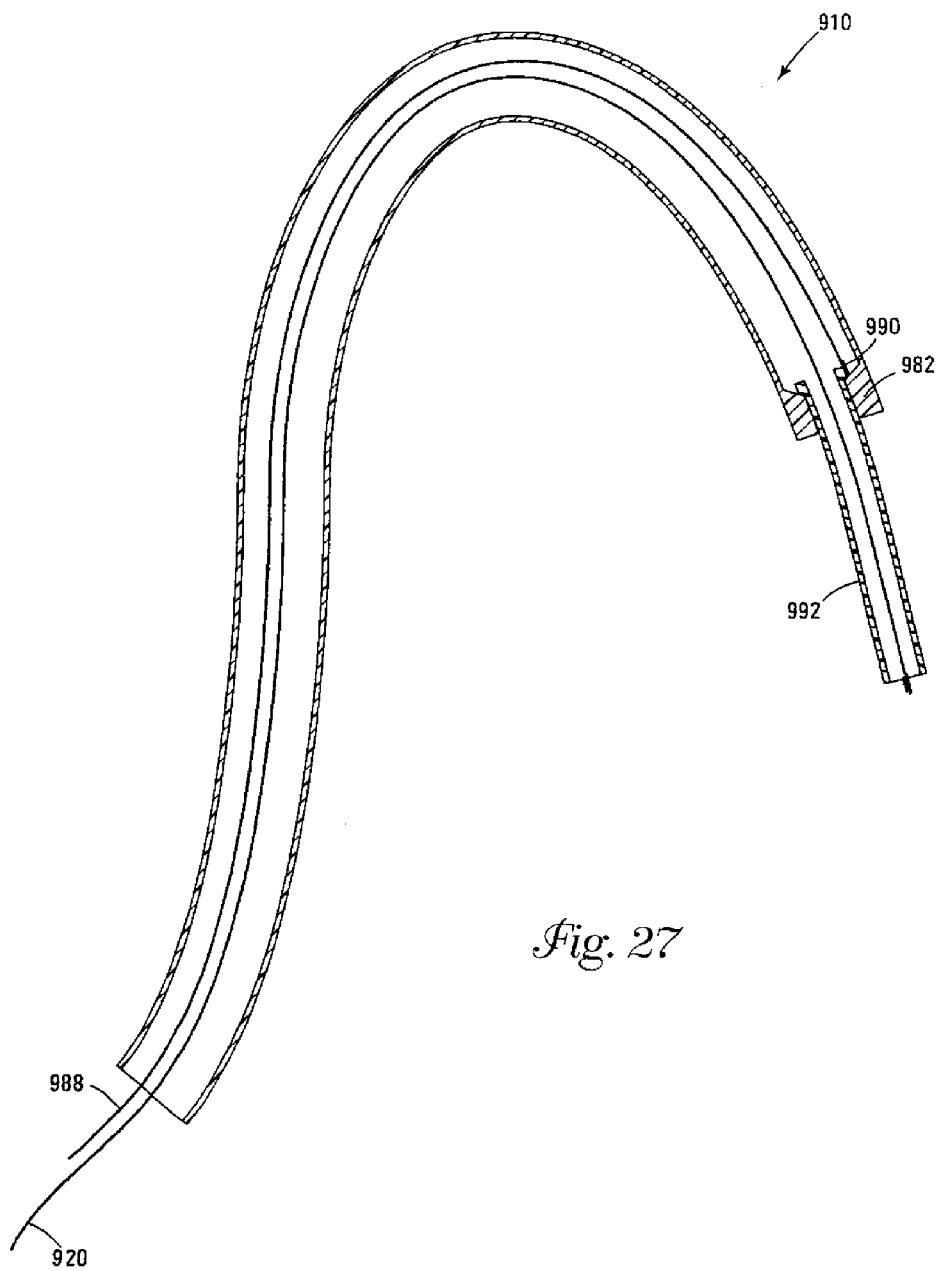
FIG. 27 is a cross-sectional view illustrating a fifth step of inserting a second guidewire into the patient through the guide catheter and outer sheath.

Once filter 22 has been drawn into outer sheath 992, the dilator 928, filter wire 20, filter 22 and collected debris can be retracted through outer sheath 992 and guide catheter 910 and removed from the patient, as shown in FIG. 26. A second guidewire 920 can be inserted through guide catheter 910 and outer sheath 992 to the site, as shown in FIG. 27.

Having thus described the embodiments of the present invention, those of skill in the art will readily appreciate other alternative embodiments that may be employed which fall within the scope of the claims attached hereto. Numerous advantages of the invention covered by this document have been set forth in the foregoing description. It should be understood that the embodiments of the present invention are exemplary only. Changes may be made in details, particularly in matters of shape, size and arrangement of parts without exceeding the scope of the invention.

What is claimed is:

1. A filter system, comprising:
   a filter wire having a proximal end and a distal end;
   a filter disposed proximal of the distal end of the filter wire;
   a shaft having a proximal end, a distal end, and a reduced inner diameter portion, wherein the shaft comprises an inner shaft having a distal end and a distal sheath extending from the distal end of the inner shaft, the reduced inner diameter portion is disposed within the distal sheath; and
   a dilator tip slidably disposable along the filter wire, said dilator tip having a plurality of recessed surfaces adapted to engage the reduced inner diameter portion of said distal sheath.

2. The filter system of claim 1, wherein said plurality of recessed surfaces includes:
   a first recessed surface disposed on a proximal portion of the dilator tip; and
   a second recessed surface disposed on the dilator tip distal said first recessed surface.

3. The filter system of claim 2, further comprising a third recessed surface disposed on the dilator tip distal said second recessed surface.

4. The filter system of claim 1, wherein the shaft limits proximal travel of the dilator tip.

5. The filter system of claim 1, wherein the dilator tip is movable between a distally advanced position in which the dilator tip extends at least partially beyond a distal end of the distal sheath and a proximally retracted position.

6. The filter system of claim 5, wherein the dilator tip comprises a conical shaped distal portion.

7. The device of claim 1, wherein the shaft comprises an inner shaft and a distal sheath, the inner shaft extending at least partially into the distal sheath, the inner shaft defining the reduced inner diameter portion.

* * * * *